United States Patent [19]
L'Esperance, Jr.

[11] 3,982,541
[45] Sept. 28, 1976

[54] EYE SURGICAL INSTRUMENT

[76] Inventor: Francis A. L'Esperance, Jr., 1 E. 71st St., New York, N.Y. 10021

[22] Filed: July 29, 1974

[21] Appl. No.: 492,575

[52] U.S. Cl. .............................. 128/303.1; 128/395; 128/275.1
[51] Int. Cl.² .................... A61B 17/36; A61M 7/00
[58] Field of Search ................. 128/6, 24 A, 275.1, 128/303.1, 303.15, 303.17, 395

[56] References Cited
UNITED STATES PATENTS

| | | | |
|---|---|---|---|
| 2,243,285 | 5/1941 | Pope | 128/6 |
| 2,243,285 | 5/1941 | Pope | 128/6 |
| 2,483,233 | 9/1949 | Price et al. | 128/17 |
| 3,710,798 | 1/1973 | Bredemeier | 128/303.1 |
| 3,732,858 | 5/1973 | Banko | 128/305 X |
| 3,736,938 | 6/1973 | Evvard et al. | 128/24 A X |
| 3,805,787 | 4/1974 | Banko | 128/24 A X |
| 3,812,855 | 5/1974 | Banko | 128/24 A X |
| 3,821,510 | 6/1974 | Muncheryan | 128/395 X |
| 3,828,780 | 8/1974 | Morrison, Jr. | 128/275.1 |

Primary Examiner—Channing L. Pace
Attorney, Agent, or Firm—Seidel, Gonda & Goldhammer

[57] ABSTRACT

Method and apparatus are disclosed for surgically removing surface portions of an eye such as cataract tissue. The eye surface portions to be removed are vaporized by a carbon dioxide laser beam. Smoke and vaporized portions are withdrawn by a vacuum pump.

17 Claims, 8 Drawing Figures

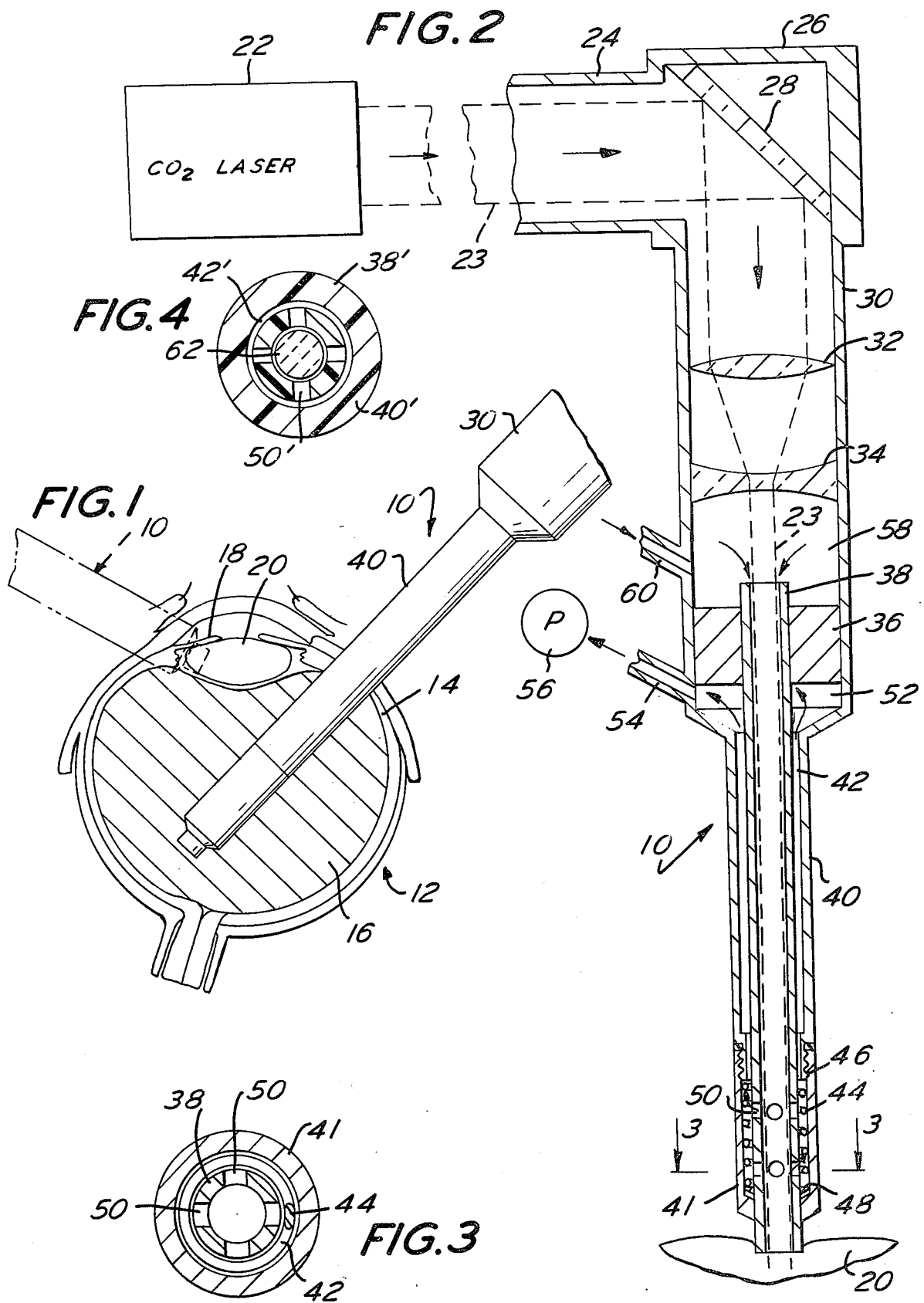

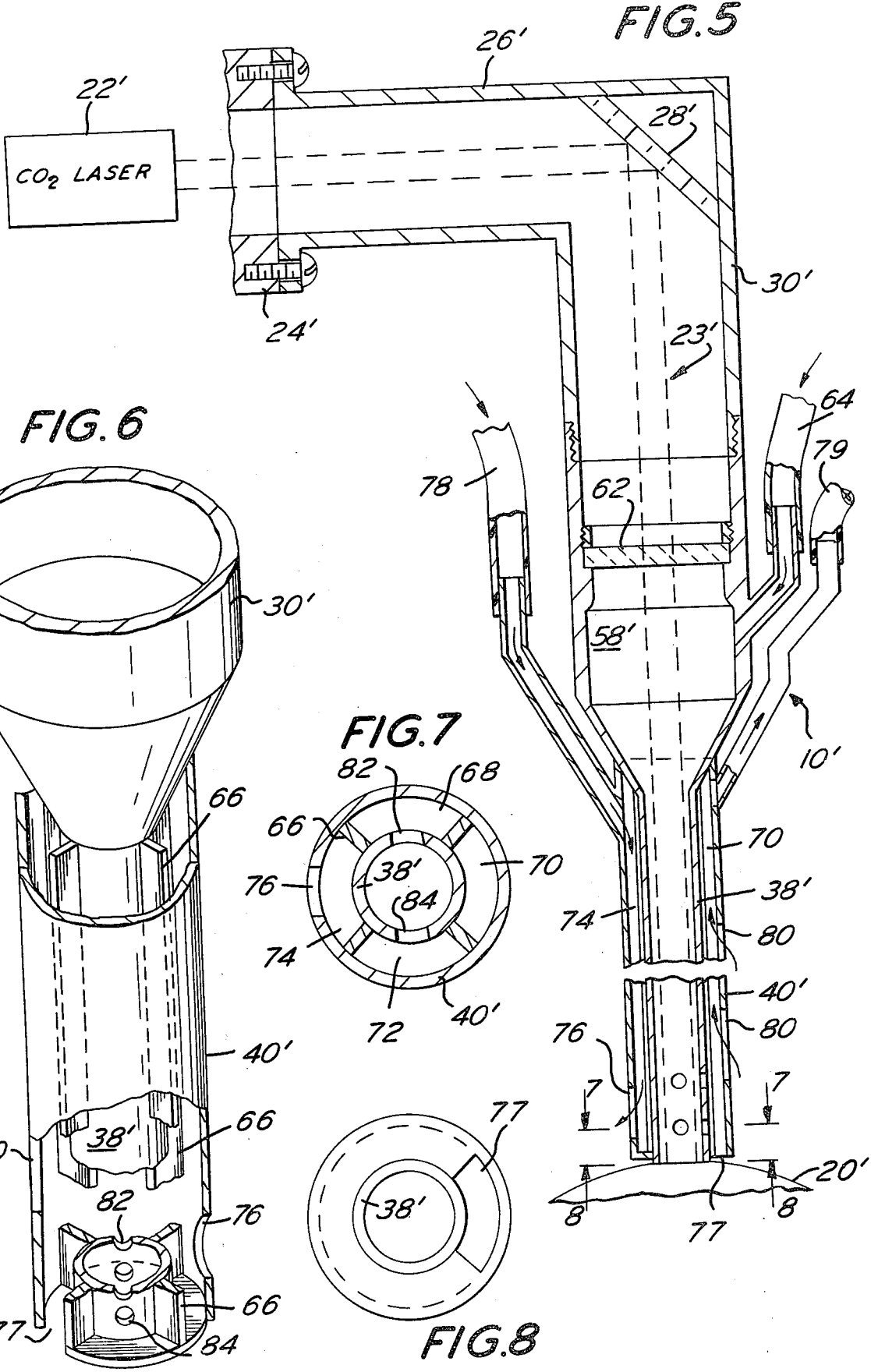

EYE SURGICAL INSTRUMENT

BACKGROUND TO DISCLOSURE

It is known to use a collimated beam of light, such as that produced by a laser, in connection with eye surgery. In such prior usage, the laser beam is directed so as to focus on the retina of the eye where the light energy is converted to heat energy. The heat energy coagulates the tissue and produces a coagulum. Eventually the coagulum turns into scar tissue and the structure that was coagulated is destroyed by virtue of the formation of scar tissue several weeks later. A device of that nature may be utilized to repair a retinal tear, or abnormal blood vessel.

DISCLOSURE

In accordance with the method of the present invention, certain portions of an eye such as cataract tissue are surgically removed. If necessary, an incision is made and a probe inserted into the incision. The probe contacts the surface of the portion to be removed. A laser beam is transmitted through the probe to the portion to be removed. A conduit means is provided for removing smoke and any vaporized portions through a passage of the probe.

Apparatus in accordance with the present invention includes a probe having a central tube open at both ends. One end of the central tube is disposed within the probe while the other end of the tube projects from the probe. A means is provided for directing a beam of collimated light through the central tube to the portion of the eye to be removed. A chamber is defined adjacent the central tube and communicates with the central tube to permit withdrawal of smoke and vaporized eye portions.

In a particular embodiment of the present invention, the source of the laser beam is preferably a carbon dioxide laser of the pulsed or continuous wave type for producing a beam of radiation in the invisible part of the spectrum at 10.6 microns wavelength. The probe is preferably in the form of a cylindrical needle having a diameter of about 2–3 mm whereby it may be introduced through a small incision through the outer layers of the eye into the inner eye. The wattage of the laser is sufficiently high so that short exposures will vaporize cataract, iris, scleral, corneal, or vitreous tissue contacted therewith. Thus, solid tissue is converted into a gas and removed through the probe to a source of low pressure such as a vacuum pump.

It is an object of the present invention to provide a novel apparatus and method for surgically removing portions of an eye such as cataracts, vitreous debris or other ocular tissue.

It is another object of the present invention to provide novel apparatus and method using a laser beam for eye surgery whereby portions of the eye to be removed are vaporized by a collimated high energy beam of light such as a laser beam.

Other objects will appear hereinafter.

For the purpose of illustrating the invention, there is shown in the drawings a form which is presently preferred; it being understood, however, that this invention is not limited to the precise arrangements and instrumentalities shown.

FIG. 1 is a diagrammatic illustration of an eye and the relationship of the instrument with respect to the same during use.

FIG. 2 is a vertical sectional view of an instrument in accordance with the present invention.

FIG. 3 is a sectional view taken along the line 3—3 in FIG. 2.

FIG. 4 is a sectional view similar to FIG. 3 but showing another embodiment.

FIG. 5 is a vertical sectional view of an instrument in accordance with another embodiment of the present invention.

FIG. 6 is a partial perspective view of the instrument in FIG. 5 with portions broken away for purposes of illustration.

FIG. 7 is a sectional view taken along the line 7—7 in FIG. 5.

FIG. 8 is an end view taken along the line 8—8 in FIG. 5.

Referring to the drawing in detail, wherein like numerals indicate like elements, there is illustrated an instrument 10 in accordance with the present invention associated with an eye designated generally as 12. In the solid line position of the instrument 10, it is extending through an incision in the outer layers of the eye into the vitreous humor 16 for vaporizing that tissue. In the phantom position of the instrument 10 shown in FIG. 1, it is orientated to extend through a small incision in the anterior outer layers of the eye for vaporizing the cataractous lens 20.

Referring to FIG. 2, a source of collimated high energy light is provided preferably in the form of a carbon dioxide laser 22 which generates a collimated beam of light or laser beam 23. The laser 22 is preferably of a nature to produce a beam 23 in pulses in the invisible part of the light spectrum at 10.6 microns wavelength. Other types of lasers may be used so long as they perform in the same manner.

The beam 23 extends through one or more articulated conduits 24 to the right angle portion 26 having a mirror 28. Mirror 28 is at an angle of about 45° with respect to the longitudinal axis of conduit 24 so that it may reflect the beam into the conduit 30. Conduit 30 may be integral with or separate from but threaded or otherwise connected to the right angle portion 26. Conduit 30 may be comprised of a plurality of sections threaded or otherwise removably secured together to facilitate supporting lenses 32 and 34 therewithin. The lens 32 is preferably a convex (positive) lens for reducing the diameter of the beam 23. Lens 34 is preferably a concave (negative) lens such as a germanium lens for stabilizing the diameter of the beam 23 to a desired diameter of about 1–2 mm. A wide variety of optics such as positive and/or negative lens can also be employed to reduce the diameter of the laser beam 23. The laser 22 preferably has sufficient power so that beam 23 below lens 34 has a power level of about 60–150 watts per square mm.

A mounting member 36 is provided within the conduit 30. Member 36 slidably guides a central tube 38 of the instrument probe which is that portion below the member 36. The diameter of the beam 23 passes entirely through the central tube 38 and has a diameter which is slightly less than the ID of the tube 38.

An outer tube 40 surrounds the central tube 38. Tube 40 may be integral with conduit 30 or separately detached therefrom in any convenient manner such as by the use of threads. The OD of tube 40 is approximately 2–3 mm. The ID of tube 40 is spaced from the OD of tube 38 to define an annular chamber 42. The outer tube 40 may be provided with a removable tip 41 as shown at the lower end of FIG. 2.

A spring 44 in chamber 42 extends from a shoulder 46 on outer tube 40 to a flange 48 on the outer periphery of the central tube 38. Spring 44 biases the flange 48 and tube 38 downwardly in FIG. 2 so that the free end of tube 38 projects from the tip 41.

The interior of central tube 38 communicates with the chamber 42 by way of a plurality of holes 50. The lower end of the annular chamber 42 is closed by the sliding contact between the tip 41 and the outer periphery of central tube 38. At its upper end, the chamber 42 communicates with chamber 52 located within the conduit 30 below member 36. A source of low pressure such as vacuum pump 56 communicates with the chamber 52 by way of conduit 54. Within conduit 30, the chamber between lens 34 and member 36 is designated 58. Chamber 58 is in open communication with the upper end of central tube 38 and communicates with a source of filtered air at atmospheric pressure by way of conduit 60.

The instrument 10 is used as follows:

Where necessary, such as for removal of the vitreous humor 16, the patient is prepared in a normal manner and an incision made in the outer layers of the eye using a scalpel. Thereafter, the probe is inserted through the incision so that the open end of central tube 38 is in contact with the vitreous humor 16 which contains vitreous opacities such as blood, membranes, or debris.

Vacuum pump 56 is turned on. A flow of air will then exit from conduit 60, through the central tube 38, through the holes 50, through chambers 42 and 52, to the vacuum pump 56. The laser beam 23 will then be generated, directed and focused as described above with a diameter of about 1-2 mm. as it passes through the central tube 38 to the surface portion of the eye tissue to be removed. The pulses of light energy vaporize the surface portion of the eye tissue to be removed. The portions vaporized and now in the form of a gas as well as smoke bubbles are removed by the air flow pattern described above in that they pass upwardly through the central tube 38, through holes 50, and through the chamber 42 to pump 56.

Cataractous lens tissue may be removed by way of a small incision in the outer wall of the eye. The free end of the tube 38 is placed adjacent to the cataractous eye lens 20 and the laser beam 23 vaporizes the cataract tissue. No other portions of the eye are damaged by the laser beam 23 due to the restrictive surface effect of laser vaporization. The spring mounting for the central tube 38 permits the probe to be kept in close contact with the target tissue to minimize escape of vaporization bubbles into the inner eye.

The particular laser beam chosen exhibits a vaporization effect which is a surface phenomenon limited to about ⅓ millimeter tissue depth and has little penetration effect. Thus, a carbon dioxide laser is preferred as compared with other visible lasers since the carbon dioxide laser beam is not transmitted through most materials, but rather absorbed causing vaporization particularly with materials that have water in them.

Manipulation of the probe relative to the patient is facilitated by articulated joints in conduits 24, which joints are per se known. If more flexibility in manipulation is desired or needed, the tubes 38 and 40 may be made of vendable polymeric plastic materials. Thus, see FIG. 4 wherein tubes 38' and 40' are constructed of such plastic materials with a flexible fiber optics bundle 62 within the entire length of central tube 38'. When using bundle 62 the laser 22 should be some type other than carbon dioxide such as argon. The construction of FIG. 4 is otherwise identical to that described above and corresponding elements have corresponding primed numerals.

In FIGS. 5–8, there is illustrated another instrument 10' in accordance with the present invention. Instrument 10' is similar to instrument 10. Hence, where appropriate corresponding primed numerals have been provided for the instrument 10' and will not be further described.

Referring to FIG. 5, it will be noted that the inner tube 38' is connected to the conduit 30'. Tube 38' does not reciprocate but may be threadedly secured to the conduit 30' if desired rather than being integral therewith.

The laser beam 23' is reduced to the proper diameter upstream of the instrument 10'. Hence, FIG. 5 does not contain an illustration of the lenses 32 and 34. A transparent partition 62 is provided to define the upper limit of chamber 58'. Filtered air under pressure is introduced into the chamber 58' by way of conduit 64. The air leaves chamber 58' by way of the open lower end of tube 38' until contact with the eye is made and then by way of apertures to be referred to hereinafter.

As shown more clearly in FIGS. 6 and 7, a plurality of ribs 66 define the space between the inner tube 38' and the outer tube 40' into chambers 68, 70, 72 and 74. Each of said chambers is approximately one quadrant.

Chamber 74 has a discharge port 76 adjacent the bottom wall thereof. A conduit 78 communicates with the upper end of chamber 74 and through which a suitable solution such as Ringer's solution may be introduced to keep the eye inflated to the proper pressure.

Chamber 70 is provided with an inlet opening 77 in the lower end thereof, the upper end of chamber 70 may be opened to the atmosphere or connected by a conduit 79 to a mechanism to control the gaseous and fluid outflow in order to regulate the intraocular pressure. Tube 40' may be provided with one or more exhaust ports 80 which communicate with chamber 70. Chamber 70 is primarily utilized to facilitate evacuation of bubbles. With respect to chambers 68–74, only chamber 70 is open at the lower end.

The lower end of tube 38' is provided with diametrically opposite apertures 82 and 84 which provide communication with the chambers 68 and 72. Each of chamber 68 and 72 communicates at its upper end with the atmosphere. The pressurized air introduced by way of conduit 64 is permitted to discharge from the center tube 38' to the chamber 68 and 72 by way of the apertures 82, 84. In this manner, smoke and debris within the inner tube 38' are evacuated by way of chambers 68 and 72.

In view of the above description with respect to instrument 10, the detailed description of operation of instrument 10' is not deemed necessary.

The present invention may be embodied in other specific forms without departing from the spirit or essential attributes thereof and, accordingly, reference should be made to the appended claims, rather than to the foregoing specification as indicating the scope of the invention.

I claim:

1. A method of surgically removing body tissue comprising the steps of contacting the body tissue with a probe open at a free end, passing a laser beam through a central passage in said probe and said open end to said tissue at a power level to effect vaporization of tissue, vaporizing only the surface portion of said tissue exposed to said laser beam in a manner so that said vaporizing step is surface phenomena at a depth not more than about one third millimeter, introducing a gas stream into the probe downstream from lenses associated with the laser beam, passing said gas stream through said probe in a direction towards said free end of said probe and out of said probe, and removing smoke and any vaporized portions of said tissue through said probe by way of said gas stream.

2. A method in accordance with claim 1 using a pulsed laser beam having a wave length in the invisible part of the spectrum.

3. A method in accordance with claim 1 including generating the laser beam with a carbon dioxide laser to produce radiation in the invisible part of the spectrum at 10.6 microns wavelength.

4. A method in accordance with claim 1 including using a probe having an outer diameter not more than three millimeters so that it may be introduced into contact with intraocular tissue.

5. A method in accordance with claim 3 including infusing a solution by way of said probe into the eye to inflate the eye and maintain the intraocular pressure.

6. Surgical apparatus for performing operations on the human body comprising a probe having a central tube disposed within an outer tube having a smooth outer surface, said central tube being open at both ends with one end disposed within the probe and the other end being exposed at a free end of the probe for contact with body tissue, means for generating a laser beam having a vaporizing surface effect on portions of the human body, means for directing said beam through said central tube, and means connected to said probe for removing smoke and any vaporized portions of tissue through the space between said tubes in a direction away from said free end of the probe.

7. Apparatus in accordance with claim 6 wherein said space includes a chamber surrounding at least part of said central tube, and means for causing air to flow through said chamber, said chamber communicating with said outer end of said central tube.

8. Apparatus in accordance with claim 6 wherein said means for generating a laser beam includes a carbon dioxide laser capable of producing a beam in the invisible part of the spectrum at 10.6 microns wavelength.

9. Apparatus in accordance with claim 6 including spring means biasing central tube in a longitudinal direction thereof toward the probe free end, said central tube being reciprocably supported by said probe against the pressure of said spring means upon contact with an object.

10. Apparatus in accordance with claim 6 wherein said central tube is supported by said probe for reciprocation in a longitudinal direction thereof, conduit means for introducing atmospheric filtered air into said one end of said central tube, a space surrounding said central tube and communicating with said other end of said central tube, vacuum means for reducing the pressure in said space.

11. Apparatus in accordance with claim 6 including fiber optics in said central tube.

12. Apparatus in accordance with claim 6 including means dividing the space between said tubes into a plurality of parallel chambers, and means for introducing a solution through one of said chambers for discharge from said one chamber adjacent said other end of said central tube.

13. Surgical apparatus in accordance with claim 6 including at least one lens associated with the laser beam, and means for introducing a stream of gas into said central tube at a location between said lens and said free end of said probe so that the gas stream is at all times downstream from said lens.

14. Surgical apparatus in accordance with claim 13 wherein the OD of said outer tube is not more than about 3 millimeters so that it may utilized in connection with surgery on intraocular tissue.

15. Surgical apparatus for performing operations on the eye comprising a probe having an inner tube, said tube being open at both ends with one end disposed within the probe and the other end being exposed at a free end of said probe, means for generating a carbon dioxide laser beam having a vaporizing effect only on the surface of eye tissue, means for directing said beam through said tube, an outer tube surrounding said inner tube and forming a part of said probe, said tubes at least in part defining at least one chamber therebetween, aperture means for providing communication between said inner tube and said chamber adjacent said other end of said inner tube, and conduit means for introducing atmospheric filtered air into said one end of said inner tube.

16. Apparatus in accordance with claim 15 includng wall means dividing the space between said tubes into a plurality of discrete chambers, one of said chambers having a port in a wall thereof adjacent said other end of said inner tube for infusion of a fluid into an eye to maintain intraocular pressure.

17. Apparatus in accordance with claim 15 wherein said probe includes a chamber for evacuation of bubbles and excess intraocular fluid.

* * * * *